United States Patent [19]

Manschot et al.

[11] 4,432,763

[45] Feb. 21, 1984

[54] FLUID DELIVERY SYSTEM AND METHOD

[75] Inventors: James G. Manschot, Eagle; Lawrence A. Salvadori, Milwaukee; David D. Plekenpol, Whitefish Bay, all of Wis.

[73] Assignee: The Kendall Company, Boston, Mass.

[21] Appl. No.: 376,382

[22] Filed: May 10, 1982

[51] Int. Cl.$^3$ .............................................. A61M 5/14

[52] U.S. Cl. .................................. 604/262; 604/410; 128/DIG. 24; 222/456

[58] Field of Search ................. 604/410, 408, 262, 77; 222/456, 454; 128/DIG. 24; 150/1

[56] References Cited

U.S. PATENT DOCUMENTS

| | | | |
|---|---|---|---|
| 3,090,532 | 5/1963 | Robson | 222/456 |
| 3,554,256 | 1/1971 | Anderson | 604/262 X |
| 3,985,135 | 10/1976 | Carpenter et al. | 604/410 |

*Primary Examiner*—Stephen C. Pellegrino

*Attorney, Agent, or Firm*—Michael, Best & Friedrich

[57] ABSTRACT

A fluid delivery system including a flexible plastic container having a filling inlet in the upper portion thereof and a feeding outlet in the lower portion thereof with a control valve to control flow from the outlet. The container is provided with a first hanger member for hanging the container on a first hanging axis. The container is further provided with a second hanger member for hanging the container on a second hanging axis which extends at right angles to the first hanging axis. The container is provided with an internal barrier means which extends from one edge of the container to a point spaced from the opposite edge of the container along a line parallel to the second hanging axis.

24 Claims, 8 Drawing Figures

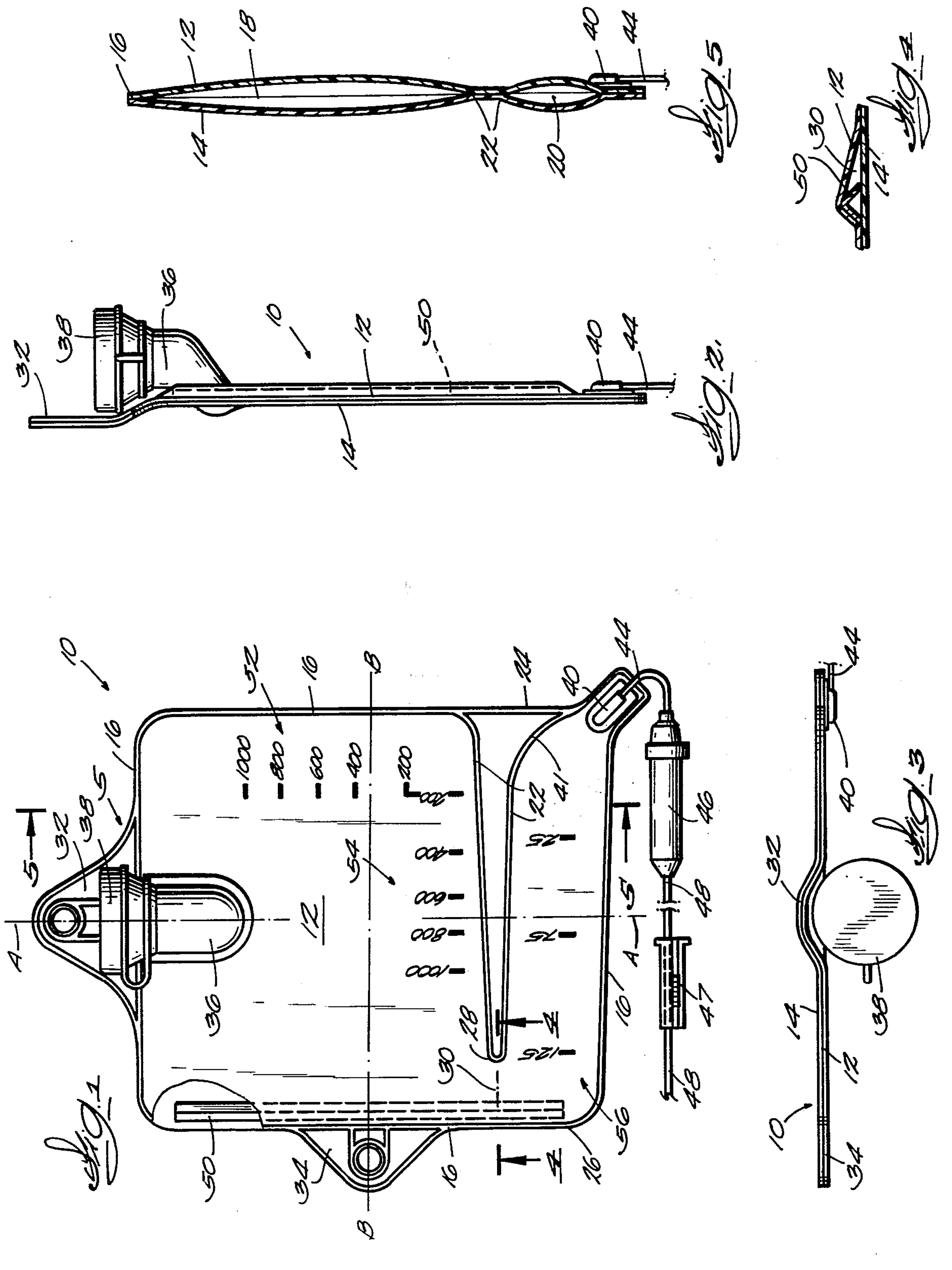

FLUID DELIVERY SYSTEM AND METHOD

BACKGROUND OF THE INVENTION

1. Field of the Invention

This invention relates to a liquid delivery system and more particularly to a liquid delivery system for enteral feeding of a patient.

2. Description of the Prior Art

In enteral feeding systems, it is desirable to be able to periodically feed given smaller amounts of diet from a larger amount of diet in a container. In prior systems, this was accomplished in one instance by continuously monitoring the flow of liquid from the container so that flow could be shut off manually after the desired amount had been fed to the patient. In another prior system, a secondary separate container is used to receive the desired amount of the limited feed portion from a primary container. Such secondary container is first filled from the primary container and then communication between the two chambers is cut off and the diet in the secondary chamber is fed to the patient. With the present invention, the need for a secondary separate container is eliminated and the system utilizes only a single plastic container which as will be explained can be easily manipulated to fed the desired limited amount of diet to a patient without the necessity of monitoring the flow by an operator once flow is initiated.

SUMMARY OF THE INVENTION

A liquid delivery system including a flexible plastic container having a filling inlet and an outlet with a control valve to control flow through the outlet. The container has a first hanger member for hanging the container in a first hanging position and a second hanger member for hanging the container in a second hanging position. The container is constructed so that when it is in its second hanging position, the interior thereof will be divided into two separate chambers wherein a portion of the liquid in the container will be in one chamber and a portion of the liquid will be in the other chamber, such two chambers when in said second hanging position having no gravity flow communication therebetween.

DESCRIPTION OF DRAWINGS

FIG. 1 is a front elevation view of the preferred embodiment of the delivery system of the present invention;

FIG. 2 is a side elevation view of the delivery system shown in FIG. 1;

FIG. 3 is a top view of the delivery system shown in FIG. 1;

FIG. 4 is a fragmentary sectional view taken along line 4—4 of FIG. 1;

FIG. 5 is a sectional view taken along line 5—5 of FIG. 1;

DESCRIPTION OF THE PREFERRED EMBODIMENT

Figure 8:
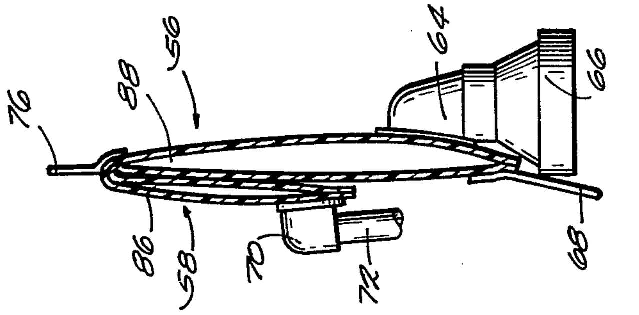
FIG. 8 is a sectional view taken along line 8—8 of FIG. 7.

Referring to the drawings in detail, the delivery container 10 shown in FIG. 1 is made of flexible plastic material preferably polyvinyl chloride. The container 10 is comprised of a front sheet 12 and a rear sheet 14 sealed along the periphial edges 16 by electronic welding or other suitable means.

Container 10 is of generally rectangular shape having an axis A—A and an axis B—B. As best shown in FIG. 5, the interior of container 10 is divided into a primary chamber 18 and a secondary chamber 20 by means of a barrier means in the form of a seal line 22. Seal line 22 extends from one edge 24 of container 10 towards the opposite edge 26 and then curves back as at 28 at a point spaced from the opposite edge 26. The seal line 22 then extends back towards edge 24 and intersects therewith. Seal line 22 provides a partial internal barrier inside container 10 to thereby form the chambers 18 and 20. Communication between chambers 18 and 20 (when in a first hanging position) is provided at an area 30 between curved end 28 of seal line 22 and edge 26 of the container.

A first hanging tab 32 is provided on axis A—A and a second hanging tab 34 is provided on axis B—B. A filling funnel and inlet port assembly 36 with a filler cap 38 is provided adjacent tab 32 on axis A—A.

An outlet port 40 is provided in the curved bottom end portion 42 of secondary chamber 20. A flexible outlet tube 44 and a drip chamber 46 is connected to outlet 40. Drip chamber 46 is connected to a flexible feeding tube 48 and an adjustable shut-off valve 47 is mounted on the tube 48.

A stabilizer member 50 is mounted inside the container along edge 26 thereof and extends from chamber 18 to chamber 20. Member 50 is secured in the desired position by fastening it to the front face 12 of the container by welding or other suitable means.

Two sets of calibrations 52 and 54 extending at right angles to each other are provided on front face 12 of the container 10 in the area of primary chamber 18. One set of calibrations 56 is provided on front face 12 of the container 10 in the area of secondary chamber 20.

As indicated previously, while the delivery system of the present invention could have several useful applications, the particular embodiment shown in the drawings and described herein is designed for enteral feeding, i.e., feeding of a patient directly into the stomach. This is normally accomplished by the use of a plastic nasal tube 49 connected to the flow control valve 47 in the system. A typical feeding procedure is as follows.

The first step is to fill the container 10 with the desired amount of nutrient material generally referred to as the "diet". This is accomplished by removing cap 38 on the inlet funnel 36 and then pouring the diet liquid into the open funnel. Valve 47 will, of course, be in its closed position when filling. Filling is performed with the container in the FIG. 1 position, i.e., with axis A—A in a vertical position. In such position, the axis of funnel 36 is also vertical, thus facilitating the filling step. After filling, cap 38 is reinstalled on the funnel inlet 36 to thereby seal the diet liquid inside the container.

Assume for purposes of explanation that 1,000 ml of diet is poured into the container. The liquid will flow into primary chamber 18 and then into secondary chamber 20 through communication space 30. Secondary chamber 20 will become completely filled and primary chanber 18 will be filled to the level indicated by the 1,000 ml calibration mark of calibrations 52.

At this point, the diet in the container can be fed to the patient in several alternative ways. If, for example, it is desired to feed the entire 1,000 ml of diet to the patient in one continuous feeding, the container is supported by hanging tab 32 with axis A—A vertical. Valve 47 is then opened and the entire diet is fed by gravity to the patient at the desired rate of flow which is determined by the adjustment of valve 47. Both chambers 18 and 20 will be completely emptied due to the gravity flow communication (when in such position) between the chambers 18 and 20 through space 30. The curved bottom portion of seal line 22 as indicated by reference numeral 41 together with the curved bottom portion 42 of secondary chamber 20 ensures complete evacuation of chamber 20. Such curved portion 42 in combination with the length of flexible tubing 44 maintains drip chamber 46 in a vertical position so that such drip chamber will operate effectively. Drip chamber 46 and feed tube 48 are shown in FIG. 1 in a horizontal position. As indicated above when in use the drip chamber and feed tube will be in a vertical position.

If it is desired to feed a smaller limited amount of the entire diet to the patient (which is often the case), the first step is to take the filled container and hang it by the use of hanger tab 34. This will place axis B—B in a vertical position. When the container is placed in this second hanging position, liquid in secondary chamber 20 will flow back into chamber 18 through communication opening 30 until the level of liquid in chamber 20 reaches 125 ml level. At this point, the liquid in chambers 18 and 20 will be separated by the vertical barrier provided by seal line 22, i.e., there will be no gravity flow communication between the chambers.

At this point, the 125 ml of diet in chamber 20 can be fed by gravity to the patient by opening valve 47. Chamber 20 will thereby be completely emptied and at the same time the balance of the initial 1000 ml of diet will remain in chamber 18. If at a later time it is desired to repeat the 125 ml feeding to the patient, valve 47 is closed and the container is then tilted to a position with axis A—A vertical. In such position, liquid will flow from chamber 18 to chamber 20 through communication opening 30. The container is then returned to its second hanging position in which event liquid in chamber 20 will assume the 125 ml level and the balance of liquid will be confined in chamber 18. The 125 ml portion of diet in chamber 20 can then be fed by gravity to the patient by opening valve 47.

If it is desired to provide a limited feed portion to the patient in an amount less than the capacity of chamber 20 (less than 125 ml), the following intermediate step is taken. With the container 10 in the second hanging position (axis B—B vertical) and the chamber 20 full (at the 125 ml level), additional liquid from chamber 20 an be forced back into chamber 18 by simply gripping the container 10 in the area of chamber 18 and then applying pressure to the sides of the chambers to thereby force liquid from chamber 20 back into chamber 18 through communication opening 30. Such pressing action is continued until the level in chamber 20 reaches the desired volume such as 100 ml, 75 ml, or some other volume less than 125 ml. This reduced amount of diet in chamber 20 can then be fed by gravity to the patient by opening valve 47.

It should be noted at this point that the presence of stabilizer member 50 which extends along edge 26 from chamber 18 to chamber 20 serves to maintain the front and rear faces 12 and 14 of the container in a spaced relationship. Such spacing will facilitate flow of liquid between chambers 18 and 20 when the container is shifted between its two hanging positions. Such spaced relation is also important to prevent any tendency of the container to fold along the barrier provided by seal line 22 to thus facilitate easy reading of the liquid levels in the respective chambers.

Figure 7:
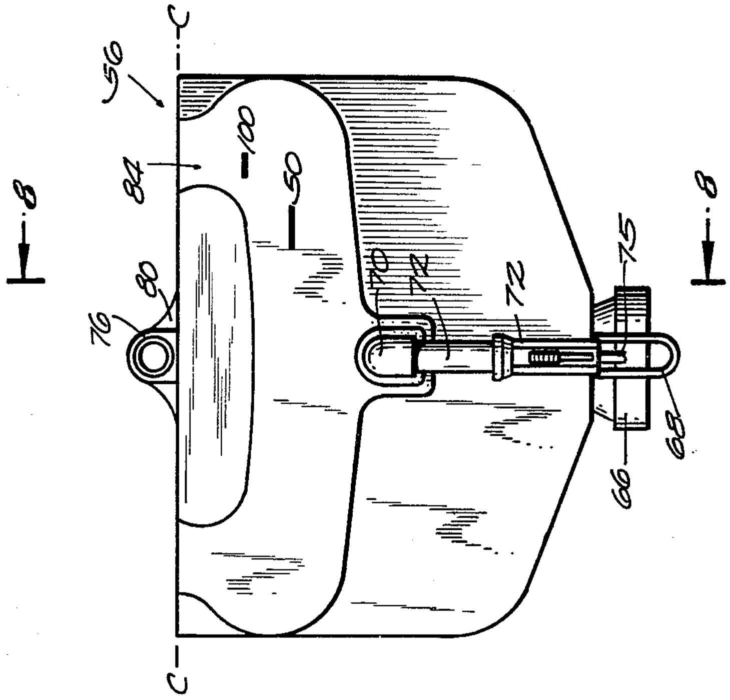
FIG. 7 is a side elevation view of the delivery system shown in FIG. 6 in a second hanging position.
Figure 6:
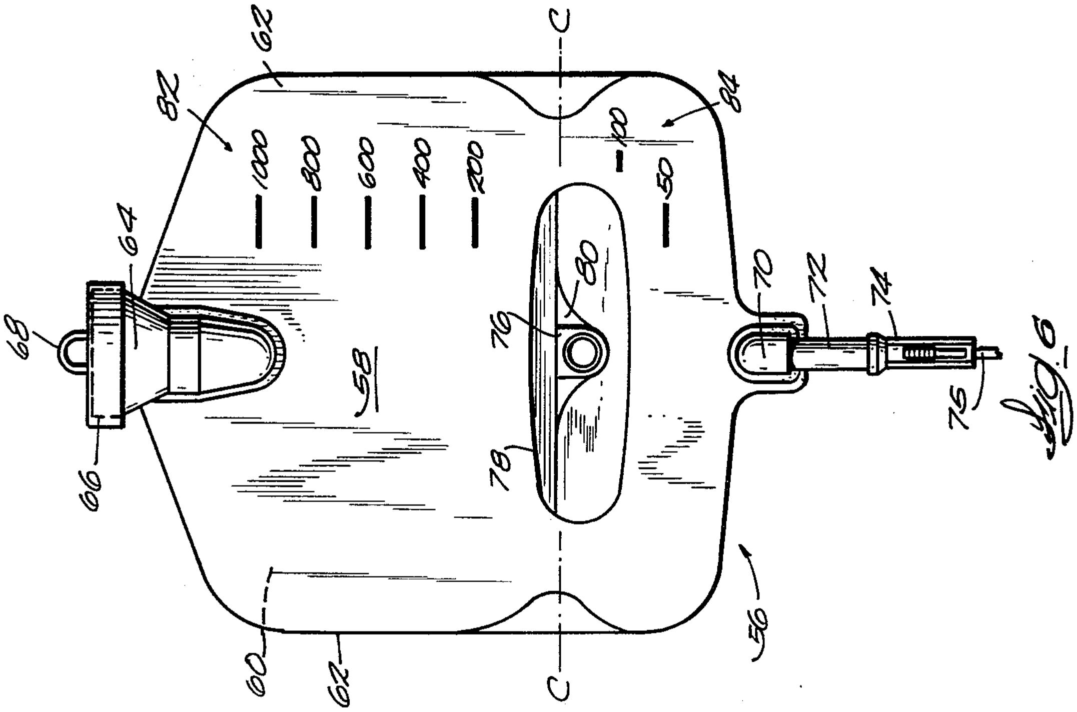
FIG. 6 is a side elevation view of a second embodiment of the present invention in a first hanging position.

A second embodiment of the invention is shown in FIGS. 6, 7 and 8. Such embodiment is comprised of a plastic container 56 having a front face 58 and a rear face 60 sealed at the periphery 62. Container 10 is provided with a filling spout 64 and a cap 66 at the top end thereof. A hanger 68 is also provided at the top of the container.

In outlet port 70, drip chamber 72, flow control valve 74 and feed tube 75 are mounted at the bottom end of container 56.

Mounted intermediate the top and bottom of container 56 is a second hanger member 76 mounted on a horizontal axis C—C. The interior of container 56 is sealed from hanger member 76 by a seal line 78 which extends around the hanger member 76. The material inside seal line 74 is cut along line 80 to allow hanger member 76 to be folded out of the plane of face 58 of container 56 for a purpose to be described hereinafter.

Two sets of calibrations 82 and 84 are provided on front face 58 of the container 56. One set 82 of calibrations is located above axis C—C and the other set 84 of calibrations is located below axis C—C.

A typical feedings procedure using the embodiment shown in FIGS. 6, 7 and 8 is as follows. The first step is to fill the container 56 with the desired amount of diet. This is accomplished by removing cap 66 on the inlet funnel 64 and then pouring the liquid diet into the open funnel. Valve 74 will, of course, be closed when filling. Filling is performed with the container in the FIG. 6 position. After filling, cap 66 is reinstalled on the funnel inlet 64 to thereby seal the diet liquid inside the container.

Assume for purposes of explanation that 1000 ml of diet is poured into the container. The interior of the container will be filled to the level indicated by the 1000 ml calibration mark of set 82 of calibration.

At this point, the diet in the container can be fed to the patient in several alternative ways. If, for example, it is desired to feed the entire 1000 ml of diet to the patient in one continuous feeding, the container is supported by first hanging member 68 in the position shown in FIG. 6. Valve 74 is then opened and the entire diet is fed by gravity to the patient at the desired rate of flow which is determined by the adjustment of valve 74.

If it is desired to feed a smaller limited amount of the entire diet to the patient (which is often the case), the first step is to take the filled container and hang it by the use of second hanger tab 76 in a position shown in FIGS. 7 and 8. In such position, the container will become folded along axis C—C to thereby form two separate chambers 86 and 88 inside the folded container 56, i.e., there will be no gravity flow communication between the two chambers. The container is tilted slightly forwardly and downwardly before folding and hanging so that after it is hung by hanging tab 76, the chamber 86 will be full up to the 125 ml level of calibrations 84.

At this point, the 125 ml of diet in chamber 86 can be fed to the patient by opening valve 74. Chamber 86 will thereby be completely emptied and at the same time the balance of the initial 1000 ml of diet will remain in chamber 88. If at a later time it is desired to repeat the 125 ml feeding to the patient, valve 74 is closed and the coontainer is returned to its FIG. 6 position. In such position, the lower portion of the container will again become filled with diet. The container is then folded and returned to its second hanging position as shown in FIGS. 7 and 8 in which event liquid in chamber 86 will assume the 125 ml level and the balance of the liquid will be confined in chamber 88. The 125 ml portion of diet in chamber 88 can then be fed to the patient by opening valve 74.

If it is desired to provide a limited feed portion to the patient in an amount less than the capacity of chamber 86 (less than 125 ml), the following intermediate step is taken. With the container in the second hanging position as shown in FIGS. 7 and 8, additional liquid from chamber 86 can be fed back into chamber 88 by simply tilting chamber 86 upwardly. Such tilting action is continued until the level in chamber 86 reaches the desired volume such as 100 ml, 75 ml or some other volume less than 125 ml. This reduced amount of diet in chamber 86 can then be fed to the patient by opening valve 74.

We claim:

1. A liquid delivery system comprising:

a container having a filling inlet in the upper portion thereof and an outlet in the lower portion thereof, said filling inlet adapted to receive a given amount of liquid poured into the interior of said container, said liquid outlet having a control valve means in fluid communication therewith to control flow from said container outlet;

a first hanger member on said container for hanging said container in a first hanging position, said container outlet when in said first hanging position being in gravity flow communication with the entire given amount of liquid in said container so that when said control valve means is opened, the entire given amount of fluid in said container will flow out of the container;

a second hanger member on said container for hanging said container in a second hanging position, said container outlet when in said second hanging position being in gravity flow communication with a portion of the entire given amount of fluid in said container so that when said control valve means is opened, only said portion of the entire given amount of fluid in said container will flow out of the container;

said interior of said container when in said second hanging position is divided into two separate chambers wherein a portion of said given amount of liquid will be contained in one of said chambers and a portion of said given amount of liquid will be contained in the other of said chambers, said two chambers when in said second hanging position having no gravity flow communication therebetween; and said two separate chambers when in said second hanging position are separated by a barrier means which extends from one edge of said container to a point spaced from the opposite edge of said container.

2. A delivery system according to claim 1 in which said container is comprised of front and rear sheets of plastic sealed to each other around the periphery thereof and said barrier means is comprised of a seal line between said front and rear sheets of plastic.

3. A delivery system according to claim 1 in which said first hanger member is mounted on a first hanging axis and said second hanger member is mounted on a second hanging axis, said first and second hanging axes being at right angles to each other.

4. A delivery system according to claim 3 in which said filling inlet is on said first hanging axis and said barrier means extends in a line parallel to said second hanging axis.

5. A liquid delivery system comprising:

a flexible plastic container having a filling inlet in the upper portion thereof and an outlet in the lower portion thereof, said filling inlet adapted to receive a given amount of liquid poured into the container, said liquid outlet having a control valve means in fluid communication therewith to control flow from said container outlet;

a first hanger member on said container for hanging said container in a first hanging position, said first hanger member located on a first hanging axis;

a second hanger member on said container for hanging said container in a second hanging position, said second hanger member located on a second hanging axis which extends at right angles to said first hanging axis;

an internal barrier means in said container extending from one edge of said container to a point spaced from the opposite edge of said container, said barrier means extending in a line parallel to said second hanging axis; and said first and second hanger members and said barrier means cooperating so that when said container is in its first hanging position said container outlet will be in gravity flow communication with the entire given amount of liquid in said container so that when said control valve means is opened the entire given amount of fluid in said container will flow out of the container, said first and second hanger members and said barrier means further cooperating so that when said container is in its second hanging position, said container will be in gravity flow communication with only a portion of the entire given amount of fluid in said container so that when said control valve means is opened only said portion of the entire given amount of fluid in said container will flow out of the container.

6. A liquid delivery system according to claim 5 in which the interior of said container when in said second hanging position will be divided into two separate chambers located on opposite sides of said barrier means so that a portion of said given amount of liquid will be contained in one of said chambers and a portion of said given amount of liquid will be contained in the other of said chambers, said two chambers when in said second hanging position having no gravity flow communication therebetween.

7. A liquid delivery system according to claim 6 in which said container is comprised of front and rear sheets of plastic sealed to each other around the periphery thereof and said barrier means is comprised of a seal line between said front and rear sheets of plastic.

8. A liquid delivery system according to claim 5 in which there is an elongated stabilizer member in said container extending along said opposite edge thereof on opposite sides of said barrier means.

9. A liquid delivery system according to claim 5 in which there are first and second sets of calibrations on the front face of said container located on opposite sides of said barrier means, said first set of calibrations extending parallel to said first hanging axis and said second set of calibrations extending parallel to said second hanging axis.

10. A liquid delivery system according to claim 9 in which there is a third set of calibrations on the front face of said container, said third set of calibrations located on the same side of said barrier means as said first set of calibrations, said third set of calibrations extending parallel to said second hanging axis.

11. A liquid delivery system according to claim 5 in which said outlet is located in the lower corner of said container at the bottom edge of the container from which said barrier means extends.

12. A liquid delivery system according to claim 11 in which the corner of the container at which said outlet is located curves downwardly.

13. A liquid delivery system according to claim 11 in which said barrier is curved at the intersection thereof with said one edge of said container.

14. A liquid delivery system comprising:

a flexible plastic container having a filling inlet in the upper portion thereof and an outlet in the lower portion thereof, said filling inlet adapted to receive a given amount of liquid poured into the container, said liquid outlet having a control valve means in fluid communication therewith to control flow from said container outlet;

a first hanger member on the upper portion of said container for hanging said container in a first hanging position, said container outlet when in said first hanging position being in gravity flow communication with the entire given amount of liquid in said container so that when said control valve means is opened, the entire given amount of fluid in said container will flow out of the container; and a second hanger member on said container located intermediate the top and bottom of the container for hanging said container in a second hanging position, said container when in said second hanging position being folded along a horizontal line to form two separate chambers, said second hanger member being attached to said container at the fold between the said two separate chambers, said container outlet when in said second hanging position being in gravity flow communication with a portion of the entire given amount of fluid in said container so that when said control valve means is opened only said portion of said given amount of fluid in said container will flow out of the container.

15. A liquid delivery system according to claim 14 in which said second hanger member is formed by a flap cut from the lower central portion of said container.

16. A liquid delivery system according to claim 14 in which there are first and second sets of calibrations on the front face of said container located on opposite sides of said second hanger member, said first and second sets of calibrations extending in a vertical direction.

17. A method of enteral feeding comprising the steps of:

(a) filling a flexible plastic container with a given amount of liquid diet with the container in a first hanging position;

(b) repositioning the container to a second hanging position wherein the liquid diet will flow into two separate chambers in said container, said two separate chambers when in said second hanging position having no gravity flow communication therebetween;

(c) feeding the diet from only one of the chambers to a patient.

18. A method of enteral feeding according to claim 17 in which the method includes the following additional steps:

(d) repositioning the container back to its first hanging position wherein the liquid diet will flow into two separate chambers in said container, said two separate chambers when in said second hanging position having no gravity flow therebetween;

(e) repositioning the container to a second hanging position wherein the liquid diet will flow into two separate chambers in said container, said two separate chambers when in said second hanging position having no gravity flow communication therebetween;

(f) feeding the diet from only one of the chambers to a patient.

19. A method of enteral feeding according to claim 18 in which the method includes the following additional steps:

(g) repeating steps (d), (e) and (f) until the entire given amount of liquid diet has been fed to the patient.

20. A liquid delivery system comprising:

a container having a filling inlet in the upper portion thereof and an outlet in the lower portion thereof, said filling inlet adapted to receive a given amount of liquid poured into the interior of said container, said liquid outlet having a control valve means in fluid communication therewith to control flow from said container outlet;

a first hanger member on said container for hanging said container in a first hanging position, said container outlet when in said first hanging position being in gravity flow communication with the entire given amount of liquid in said container so that when said control valve means is opened, the entire given amount of fluid in said container will flow out of the container; and a second hanger member on said container for hanging said container in a second hanging position, said container outlet when in said second hanging position being in gravity flow communication with a portion of the entire given amount of fluid in said container so that when said control valve means is opened, only said portion of the entire given amount of fluid in said container will flow out of the container;

said interior of said container when in said second hanging position is divided into two separate chambers wherein a portion of said given amount of liquid will be contained in one of said chambers and a portion of said given amount of liquid will be contained in the other of said chambers, said two chambers when in said second hanging position being separated by a barrier means, said barrier means positioned between said two separate chambers and serving to prevent gravity flow of liquid between said two separate chambers when said container is in said second hanging position.

21. A liquid delivery system according to claim 20 in which said barrier means extends from one edge of said container to a point spaced from the opposite edge of said container.

22. A liquid delivery system according to claim 21 in which said container is comprised of front and rear sheets of plastic sealed to each other around the periphery thereof and said barrier means is comprised of a seal line between said front and rear sheets of plastic.

23. A liquid delivery system according to claim 20 in which said container when in said second hanging position is folded along a horizontal line to form two separate chambers, said second hanger member being attached to said container at the fold between said two separate chambers.

24. A liquid delivery system according to claim 23 in which said second hanger member is formed by a flap cut from the lower central portion of said container.

* * * * *

UNITED STATES PATENT AND TRADEMARK OFFICE
CERTIFICATE OF CORRECTION

PATENT NO. : 4,432,763

DATED : February 21, 1984

INVENTOR(S) : James G. Manschot, Lawrence A. Salvadori, David D. Plekenpol

It is certified that error appears in the above—identified patent and that said Letters Patent is hereby corrected as shown below:

Column 1, Line 26, After "to" and before "the" delete "fed" and substitute therefor ---feed---

Column 2, Line 3, After "the" and before "edges" delete "periphial" and substitute therefor ---peripheral---

Column 3, Line 52, After "chamber 20", delete "an" and substitute therefor ---can---

Column 4, Line 28, After "typical" and before "procedure", delete "feedings" and substitute therefor ---feeding---

Line 68, Before "is", delete "coontainer" and substitute therefor ---container---

Signed and Sealed this

*Seventeenth* Day of *July 1984*

[SEAL]

*Attest:*

GERALD J. MOSSINGHOFF

*Attesting Officer* *Commissioner of Patents and Trademarks*